(12) United States Patent
Oberholtzer et al.

(10) Patent No.: US 6,268,351 B1
(45) Date of Patent: Jul. 31, 2001

(54) METHODS FOR INDUCING PROLIFERATION IN AUDITORY RECEPTOR EPITHELIUM

(75) Inventors: J. Carl Oberholtzer; Dhasakumar S. Navarathan, both of Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/077,264

(22) PCT Filed: Sep. 26, 1997

(86) PCT No.: PCT/US97/17428
§ 371 Date: May 27, 1998
§ 102(e) Date: May 27, 1998

(87) PCT Pub. No.: WO98/13048
PCT Pub. Date: Apr. 2, 1998

(51) Int. Cl.[7] .............................. A01N 43/04; A61K 31/70
(52) U.S. Cl. .............................. 514/46; 514/47; 424/1.73; 424/9.35; 424/9.351; 424/9.6; 424/70.1; 435/6
(58) Field of Search .................................. 424/1.73, 9.35, 424/9.351, 9.6, 70.1; 435/6; 514/46, 47, 880

(56) References Cited

U.S. PATENT DOCUMENTS

| | | | |
|---|---|---|---|
| 5,017,368 | * | 5/1991 | Sugiyama et al. .................. 424/70.6 |
| 5,527,772 | * | 6/1996 | Horlick . |
| 5,529,769 | * | 6/1996 | Cho et al. . |
| 5,837,681 | * | 11/1998 | Magal . |
| 5,840,690 | * | 11/1998 | Horlick . |
| 6,066,618 | * | 5/2000 | Horlick . |
| 6,136,785 | * | 10/2000 | Corwin et al. . |

OTHER PUBLICATIONS

Douglas A. Cotanche, et al. Hair cell regeneration in the bird cochlea following noise damage or ototoxic drug damage. *Anatomy and Embryology*. 1994 189: 1–18.

Hiroshi Yamashita, et al. Induction of cell proliferation in mammalian inner–ear sensory epithelia by transforming growth factor α and epidermal growth factor. *Proc. Natl. Acad. Sci. USA*. Apr. 1995 92: 3152–3155.

J. Lisa Zheng, et al. Induction of Cell Proliferation by Fibroblast and Insulin–Like Growth Factors in Pure Rat Inner Ear Epithelial Cell Cultures. *The Journal of Neuroscience*. Jan. 1, 1997 17(1): 216–226.

Jeffrey T. Corwin, et al. Regeneration of Sensory Hair Cells After Acoustic Trauma. *Science*. Jun. 1998 240: 1772–1774.

Jennifer S. Stone, et al. Identification of the Timing of S Phase and the Patterns of Cell Proliferation During Hair Cell Regeneration in the Chick Cochlea. *The Journal Of Comparative Neurology*. 1994 341:50–67.

Paul R. Lambert, M.D. Inner Ear Hair Cell Regeneration in a Mammal: Identification of a Triggering Factor. *Laryngoscope*. Jun. 1994 104: 701–718.

* cited by examiner

*Primary Examiner*—James O. Wilson
(74) *Attorney, Agent, or Firm*—Dann, Dorfman, Herrell and Skillman

(57) ABSTRACT

The present invention provides novel methods for stimulating proliferation in auditory receptor epithelium. Administration of agents that activate cAMP production result in demonstrable regeneration of hair cells in the cochlea. These agents may be administered in vivo to restore hearing loss or balance loss in patients in need of such treatment.

19 Claims, 4 Drawing Sheets

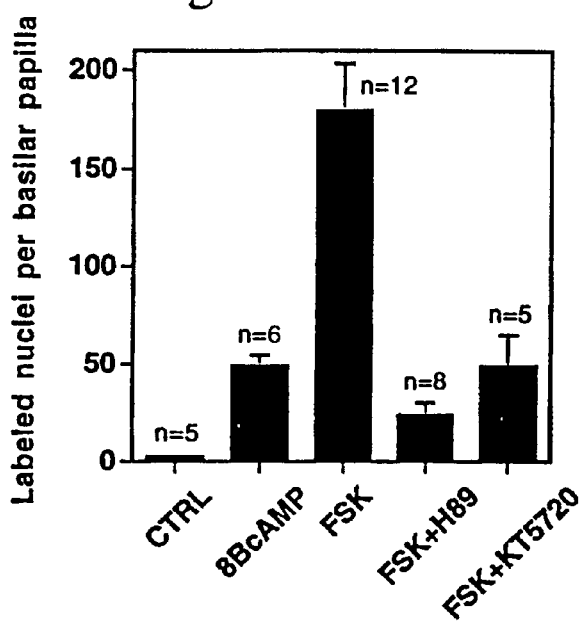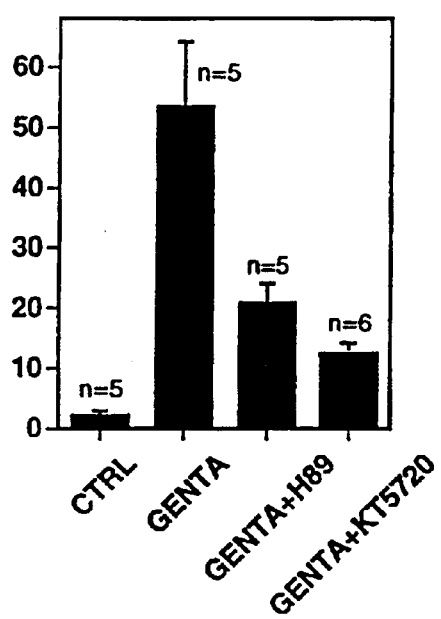
Fig. 2A
Fig. 2B

METHODS FOR INDUCING PROLIFERATION IN AUDITORY RECEPTOR EPITHELIUM

Pursuant to 35 U.S.C. §202(c) it is acknowledged that the U.S. Government has certain rights in the invention described herein, which was made in part with funds from the National Institutes of Health, Grant Numbers K08DC00069 and R01DC02755.

FIELD OF THE INVENTION

This invention relates to the field of auditory research. Specifically, the invention pertains to methods which promote the regeneration of auditory hair cells following loss due to trauma or disease.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference herein.

Hair cells are sensory cells that transduce motion into neural signals. In the cochlea, they are used to detect sound waves in the environment and convert them into auditory signals that can be processed in the brain. Loss of receptor hair cells in the cochlea accounts for a significant proportion of hearing impairment in the population (1). This loss can occur as a consequence of viral or bacterial insult, aging, and damage from intense sound or aminoglycoside antibiotics. The generation of replacement hair cells following damage by sound or drugs has been clearly demonstrated in birds (2–4), the chick being the best-studied model for auditory hair cell regeneration (5). New hair cells arise as progeny from an otherwise non-dividing supporting cell population induced to proliferate by the damage (6–12). Functional recovery of hearing accompanies this cellular recovery process (13,14). The signals and pathways responsible for regenerative proliferation are presently unknown. However, evidence in the art indicates that such a regenerative response also occurs in mammals.

SUMMARY OF THE INVENTION

The present invention provides a novel system for the regeneration of auditory receptor hair cells. The generation of replacement hair cells following damage by sound or drugs has been clearly demonstrated in birds where the hair cells arise from a normally non-dividing supporting cell population induced to proliferate by the damage. The present invention demonstrates that agents which increase cAMP levels induce cell proliferation in explanted but otherwise undamaged receptor epithelium of cochleas, and that protein kinase A (PKA) inhibitors block this proliferative response. Furthermore, the proliferative response which follows in vitro gentamicin damage is also significantly blocked by PKA inhibitors. Accordingly, biochemical manipulation of the cAMP pathway is now possible. Thus, in one embodiment of the invention, a research tool is provided for the elucidation of the molecular events involved in the restoration of auditory receptor hair cells. In a preferred embodiment, stimulation of proliferation is achieved via the administration of agents which activate the cAMP pathway, such as stimulators of adenylate cyclase (i.e., forskolin). Forskolin may be used in a range of about 1–200 $\mu$M. Narrower ranges of forskolin concentration are also contemplated in practicing the present invention, i.e, between about 10 $\mu$M–100 $\mu$M, or between about 75 $\mu$M–150 $\mu$M. Alternatively, cAMP levels may be augmented by direct delivery of cAMP or analogues thereof (i.e., 8-Br-cAMP). Proliferation of auditory receptor cells may be assessed by co-administration and detection of agents that are incorporated into replicating DNA (i.e., Bromo-deoxyuridine).

In another embodiment, the explant cochlea cultures are exposed to ototoxic agents. Damage to these cultures results in a proliferative response. Following damage, this regenerative response may be abrogated by agents that inhibit the cAMP mediated signal transduction pathway, such as PKA inhibitors. The culture systems of the present invention therefore provide a valuable research tool for dissecting the signal transduction pathway responsible for the restoration of hearing loss.

In yet another embodiment of the invention, a method for treating a patient suffering from hearing loss is provided. The term "patient" as used herein may be a human or an animal subject. The method comprises delivering to a patient's auditory receptor epithelium, a cAMP activating agent in a suitable pharmaceutical carrier in an effective amount to activate the signal transduction pathway responsible for regeneration of hair cells in the cochlea epithelium. In an alternative embodiment of the invention, the method is used to assess the regeneration of hair receptor cells in the bird. In this embodiment, an agent for detecting DNA replication is co-administered to the damaged auditory epithelium with the cAMP pathway activating agent. Following stimulation of a proliferative response, the animal is sacrificed and the level of proliferation assessed.

The following definitions are provided to facilitate the understanding of the subject matter of the present invention:

Receptor hair cells are cells which lie in the upper part of the epithelium with their stereocilia embedded in the tectorial membrane. Hair cells are surrounded by supporting cells. The transduction of the mechanical energy of sound to a coded neural signal is effected by hair cells. Receptor hair cells are located in the sensory epithelia of both the auditory and vestibular portions of the inner ear.

The vestibular system is composed of the utricle, the saccule and the three ampullae of the semicircular canals. Impairments in the vestibular sensory epithelia often cause impaired balance.

The auditory receptor epithelia is located within the cochlea and is referred to the organ of corti in mammals and basilar papilla in avian species. Damage to the sensory epithelium in the cochlea can lead to impaired hearing.

The methods of the invention provide a novel approach for stimulating the regeneration of auditory receptor epithelium. The methods of the present invention may be beneficially used to elucidate the molecular mechanisms relevant in the restoration of hearing in subjects whose hearing has been damaged due to trauma or disease.

BRIEF DESCRIPTION OF THE DRAWINGS

FIGS. 1A–1C; Control whole-mounts fluorescently stained for filamentous actin with rhodamine-labeled phalloidin. The cochlea shown in (FIG. 1A) and (FIG. 1B) was fixed and stained immediately following removal; the explant shown in (FIG. 1C) was maintained in culture with no other treatment for 3 days prior to staining. p and d identify the proximal (basal) and distal (apical) ends of the basilar papilla; n and a indicate the neural (superior) and abneural (inferior) aspects. Se indicates the sensory epithelium in which the stereocilia bundles of the receptor hair cells can be identified. FIGS. 1D–1G; Whole-mounts immunochemically stained for BrdU (purple-black). In these panels the position of the exposed sensory epithelium is outlined with dashed white lines. FIG. 1H, FIG. 1I; Cross-sections immunostained for both BrdU (purple-black) and for calbindin (brown), to highlight the sensory epithelium. Explants were treated with forskolin (FIG. 1D) and (FIG. 1H), or forskolin plus PKA inhibitor KT5720 (FIG. 1E); and damaged with gentamicin (FIG. 1F), or damaged with gentamicin and treated with PKA inhibitor H89 (FIG. 1G). Control explants are shown in (FIG. 1I), as well as in (FIGS. 1A–1C). Arrows in (FIG. 1D) indicate doublets or clusters of BrdU-labeled nuclei. In panel (FIG. 1H) the arrowhead indicates a labeled nucleus at the supporting cell level while the arrow indicates labeled nucleus at receptor hair cell level; arrow in inset indicates vertical cluster of labeled nuclei. In panel (FIG. 1I) the arrows indicate a fold or bend in the sensory epithelium which was introduced in the explant during the period of culture. The lower arrow points to the basilar membrane, while the upper arrow points to the tectorial membrane. Note that cells outside the sensory epithelium were also labeled with BrdU, however their labeling is independent of forskolin treatment. DNA synthesis in these cell types, many of which are likely to be fibroblasts, is either constitutive or was induced by explantation alone. Calibration bars: 0.2 mm in (FIGS. 1A–1G); 50 $\mu$m in (FIG. 1H, FIG. 1I).

FIGS. 2A and 2B are graphs summarizing the data showing the involvement of the cAMP pathway in signaling proliferation in the undamaged and gentamicin-damaged auditory receptor epithelium. Bars show the mean number of labeled nuclei per sensory epithelium for each of the indicated groups. Error bars are the standard error of the mean (S.E.M.); n is the number of cochleas per group. FIG. 2A shows results from undamaged cochlear explants receiving no treatment (CTRL); or treatment with 8-bromo-cAMP and IBMX (8BcAMP), forskolin (FSK), forskolin plus PKA inhibitor H89 (FSK+H89), or forskolin plus PKA inhibitor KT5720 (FSK+KT5720). [ANOVA; $F4,31=18.181$ ($p<0.001$)]. Significantly different individual comparisons are: CTRL vs. FSK, FSK vs. FSK+H89, FSK vs. FSK+KT5720, and 8BcAMP vs. FSK. The somewhat smaller effect of 8-bromo-cAMP as compared to forskolin may reflect a less robust stimulation of the cAMP pathway (see for example references 24, 25). FIG. 2B shows results from explanted cochleas receiving no treatment (CTRL), or damaged with gentamicin (GENTA), damaged with gentamicin and treated with PKA inhibitor H89 (GENTA+H89), and damaged with gentamicin and treated with PKA inhibitor KT5720 (GENTA+KT5720). [ANOVA; $F3,17=16.208$ ($p<0.001$)]. Significantly different individual comparisons are: CTRL vs. GENTA, GENTA vs. GENTA+H89, and GENTA vs. GENTA+KT5720. The lack of a complete block of DNA synthesis by PKA inhibitors in these settings may be due to partial cellular accessibility of the inhibitors, or may indicate the involvement of additional mechanisms.

FIG. 3A shows a portion of sensory epithelium of one cochlear explant with the tectorial membrane (t), basilar membrane (b), and innervating fibers (n) identified. FIG. 3B and FIG. 3C show segments of the sensory epithelia of two additional cochlear explants. $^3$H-thymidine-labeled sensory hair cells are marked with arrows. These are identified as hair cells on the basis of their shapes, their characteristic dark-staining cytoplasm, and their flat apical surfaces forming part of the reticular lamina. Magnification 500x.

FIG. 4A: ear canal; FIG. 4B: middle ear; FIG. 4C: oval window; FIG. 4D: semicircular canal; FIG. 4E: utricle; FIG. 4F: pinna; FIG. 4G: eardrum; FIG. 4H: round window; FIG. 4I: eustachian tube; FIG. 4J: saccule; FIG. 4K:

DETAILED DESCRIPTION OF THE INVENTION

Figure 1A:
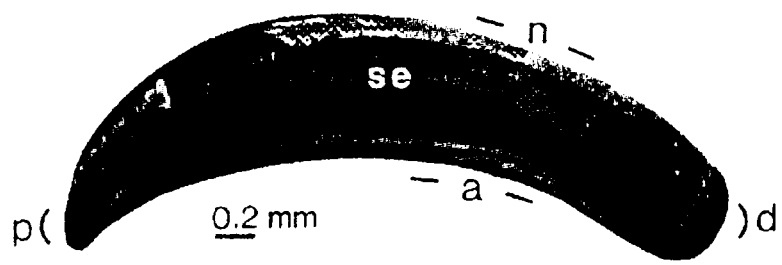
FIGS. 1A–1I are a series of micrographs depicting cochlear explants cultured in the presence of BrdU and exposed to forskolin with/without PKA inhibitors, or damaged with gentamicin with/without PKA inhibitors.

In eucaryotic cells, cyclic AMP serves as a second messenger which is produced as a result of the activation of cell-surface receptors. The present invention demonstrates that proliferation may be induced in undamaged receptor epithelium by agents which increase cAMP levels, and that following this stimulation, hair cells become labeled with proliferation markers. This remarkable proliferative response is blocked by inhibitors of the cAMP-regulated protein kinase (PKA). In addition, the results presented illustrate that the proliferative response induced by in vitro gentamicin damage is also significantly blocked by PKA inhibitors. These observations are the first to identify a signaling pathway which plays a role in regenerative proliferation in the auditory receptor epithelium. Accordingly, activation of this pathway can now be accomplished via the administration of stimulatory agents to the auditory receptor epithelium.

The present invention provides a valuable research tool for the elucidation of the molecular events relevant to the restoration of hearing in patients who have lost receptor epithelium hair cells. Now that the cAMP pathway has been identified as playing a key role in regeneration of the receptor epithelium in the cochlea, it is possible to biochemically intervene at several points in the pathway and characterize the key steps leading to proliferation. In a preferred embodiment, a cell line will be developed to provide a continuous culture system to study the signal transduction events which result in the regeneration of hair cells.

Gentamicin treatment of acute gram negative infections leads to significant loss of receptor hair cells in humans. Restoration of hearing in these patients by topical administration of agents that stimulate the cAMP pathway may now be possible. Similarly, chemotherapies used in cancer treatment also damage the hair cells in the auditory receptor epithelium. Acoustic trauma and aging also result in hearing loss. In situ administration of agents that affect the cAMP pathway may be effective in restoring hearing in these patients.

MATERIALS AND METHODS

A. Cochlear Explant Cultures.

Cochleas were removed carefully under sterile conditions and maintained in free-floating culture in DMEM with 10% fetal calf serum for 3–4 days in 5% $CO_2$ at 37° C. (11,20). 5-bromo-2-deoxyuridine (BrdU; Sigma) was included at 0.01% to mark those cells undergoing DNA synthesis. The following agents were dissolved in dimethyl sulfoxide (DMSO) and added to the culture medium at the indicated concentrations: Forskolin (100 $\mu$M), H89 and KT5720 (each at 0.5 $\mu$M; from Calbiochem), and isobutyl methylxanthine (IBMX; 0.5 mM). 8-bromo-cAMP was added to a final concentration of 5 mM from an aqueous stock solution. Control cultures included carrier DMSO at a final concentration (1%) similar to that present in the experimental cultures. Negative controls for forskolin were performed using the inactive analog 1,9-dideoxy-forskolin (100 $\mu$M; Calbiochem); this compound did not stimulate DNA synthesis (data not shown). Those explants treated with 8-bromo-cAMP were pretreated for 24 hours with IBMX, and IBMX was maintained in the medium throughout the three days 8-bromo-cAMP was present. PKA inhibitors (H89 and KT5720) were added to the medium 1 day prior to the addition of either forskolin or gentamicin, and maintained at the same concentration throughout the duration of the experiments. Gentamicin sulfate was added to explant cultures at a final concentration of 0.1% (20,21). Cochleas used for autoradiography were maintained for five days in culture in the presence of forskolin and $^3$H-thymidine (1 $\mu$Ci/ml; 20 Ci/mmol). For all explant cultures one-half of the medium, including all additives, was replaced daily.

B. Detection of BrdU.

Nuclear BrdU incorporation was determined in whole-mounts essentially as described (11). Briefly, cochleas were immobilized on a matrix (Silguard) and the tegmentum vasculosum was dissected away. The tectorial membrane was peeled away after a 5 minute treatment with 0.005% subtilisin (Sigma type 27). Cochleas were then immersed in 10% normal buffered formalin for 30 minutes followed by a 20 minute incubation in 2N HCl, 0.1% Tween 20. BrdU was detected immunohistochemically by incubating the cochleas in the presence of anti-BrdU antibody (Becton Dickinson) for one hour (1:40 in PBS, 0.1% Tween 20) followed by secondary antibody (1:1000 alkaline phosphatase-conjugated goat anti-mouse, Boehringer Mannheim) for an additional hour. Secondary antibody was detected with 5-bromo-4-chloro-3-indolyl phosphate (0.34 mg/ml) and nitro-blue tetrazolium (0.175 mg/ml) in 100 mM NaCl, 50 mM $MgCl_2$, 100 mM Tris-HCl pH 9.5. Cochleas were washed three times in PBS, 0.1% Tween 20 between each step. Fluorescent staining for filamentous actin in cochlear whole-mounts was performed using rhodamine-labeled phalloidin as previously described (22).

C. Tissue Processing.

Tissue cross-sections were prepared from cochleas embedded in paraffin for immunohistochemistry, and in plastic for autoradiography. Paraffin sections (5 $\mu$m-thick) were cut from cochleas that were fixed for 24 hours in Bouin's fixative, dehydrated, and embedded. These were stained with anti-BrdU antibodies (see above) after deparaffination. In order to highlight the sensory epithelium in the paraffin sections they were also stained immunohistochemically for calbindin D28K23 using a procedure similar to that for BrdU. The primary antibody was a rabbit anti-calbindin antiserum (1:500 in PBS, 0.1% Tween 20) which was detected with a goat anti-rabbit antibody (1:1000) coupled to horseradish peroxidase using 3,3'-diaminobenzidine and $H_2O_2$ as substrates. One $\mu$m-thick plastic sections for autoradiography were cut from cochleas fixed in 2% glutaraldehyde overnight at 4° C. and then for one hour in fixative with 1% tannic acid, followed by dehydration and embedding in Epon. Plastic sections were coated with undiluted NTB-2 emulsion (Eastman-Kodak, Rochester). Slides were developed (Kodak D19) and fixed (Kodak Rapid Fixer) after 4 days exposure at 4° C. The tissue sections were then counterstained with 1% Toluidine Blue.

D. Statistics.

Whole-mounts of cochlear explants cultured in the presence of BrdU were examined with darkfield illumination (see FIG. 1). For consistency a single observer, blinded to the treatment groups, performed all counts. The number of single, clearly-BrdU-labeled nuclei within the sensory epithelium was determined for each explant. In general, the intra-epithelial location of labeled nuclei was easily determined by adjusting the level of focus. Nuclei not unambiguously within the epithelium were not counted. Multivariate analysis was performed by one way ANOVA followed by multiple comparisons with the Student-Newmans-Keuls method (SigmaStat for Windows; Jandel Corporation, San Rafael, Calif.). Results are shown in FIG. 2 as the mean±S.E.M. A difference between groups of $p<0.05$ was considered statistically significant.

E. Mammalian Utricle Cultures

Utricles may be prepared as described in (26). Briefly, utricular epithelial sheets are separated from postnatal day 4–5 Wistar rats with 0.5 mg/ml thermolysin (Sigma, St. Louis, Mo.) in calcium- and magnesium-free Hanks buffered saline solution for 30 minutes at 37° C. The epithelial sheets are then incubated in a mixture of 0.125% trypsin and 0.125% collagenase for 8 minutes at 37° C. The enzyme activity was inactivated with a mixture of 0.005% soybean trypsin inhibitor (Sigma) and 0.005% DNase (Worthington, Freehold, N.J.) before being pipetted up and down with a 1 ml pipette tip 10 times in BMEM. In this way the epithelial sheets were partially dissociated into small pieces containing 10–80 cells. These cells grow poorly in serum free media, therefore the medium was supplemented with 5% fetal bovine serum. The cell suspension was then plated in poly-D-lysine-coated (500 $\mu$g/ml) 96 well plates or 16 well labtek slides in 200 $\mu$l of serum containing medium (DMEM+5% fetal bovine serum, 4.5 mg/ml glucose, 2 mM glutamine, 25 ng/ml fungizone, and 10 U/ml penicillin) at a density of approximately 70 cells/mm$^2$.

EXAMPLE I cAMP Plays a Role in Stimulating Proliferation of Auditory Receptor Epithelium In initial differential PCR-based studies performed to identify genes whose expression changes during regenerative proliferation in the chick auditory receptor epithelium following gentamicin damage, a cDNA fragment was isolated which was homologous to phosphodiesterase. The upregulation during proliferation in the sensory epithelium of an enzyme which functions to breakdown the second messenger cAMP suggested that this might represent a homeostatic mechanism by which a mitogenic signal is terminated. To test the hypothesis that the cAMP-dependent pathway plays a role in signaling regenerative proliferation in this system, a series of experiments were carried out using various agents which specifically stimulate or block this pathway. These agents were applied to cochlear explants in short-term culture, and proliferation in the sensory epithelium was assayed using the DNA synthesis markers 5-bromo-2-deoxyuridine (BrdU) and $^3$H-thymidine.

The first set of experiments was performed using undamaged cochleas. Five groups of cochleas were explanted from four day-old chicks and immediately placed in culture in the presence of BrdU. The first group was treated with no additional pharmacological agent, and served as a control. The second group was treated with the adenyl cyclase activator forskolin in order to increase cAMP levels. The third group was treated with the membrane-permeable cAMP analog 8-bromo-cAMP and the phosphodiesterase inhibitor iso-butyl methylxanthine (IBMX) as an independent method of activating the cAMP pathway. The fourth group was treated with both forskolin and the specific PKA inhibitor H89. The fifth group was treated with both forskolin and the specific PKA inhibitor KT5720. Groups four and five were included to confirm that any proliferative response was mediated by PKA, the major cAMP pathway effector. After incubation for three days, cochleas were fixed and whole mounts examined for BrdU incorporation using immunohistochemistry.

Figures 1B, 1C:
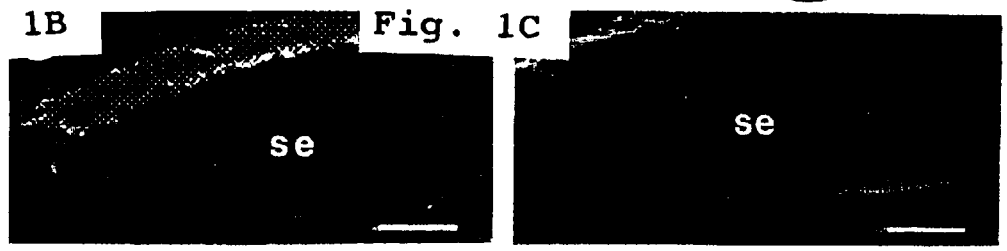

Shown for orientation purposes in FIG. 1A is a freshly-dissected chick cochlea from which the tegmentum vasculosum and tectorial membrane have been removed revealing the surface of the sensory epithelium (labeled "se"); FIG. 1B shows a portion of this sensory epithelium (basilar papilla) at higher power. The stereocilia bundles on the apical surfaces of the receptor hair cells can be seen studding the epithelium in this preparation stained to reveal filamentous actin using fluorescence-labeled phalloidin. A similar preparation of a cochlea maintained in culture for three days is shown in FIG. 1C. A measure of the integrity of the sensory epithelium maintained under the culture conditions used for these experiments can be determined by examining the preserved precise array of receptor hair cells across the papilla. The similar whole-mount preparations shown in panels D–G, stained immunohistochemically for BrdU, are presented at a comparable magnification.

Figures 1D, 1E:
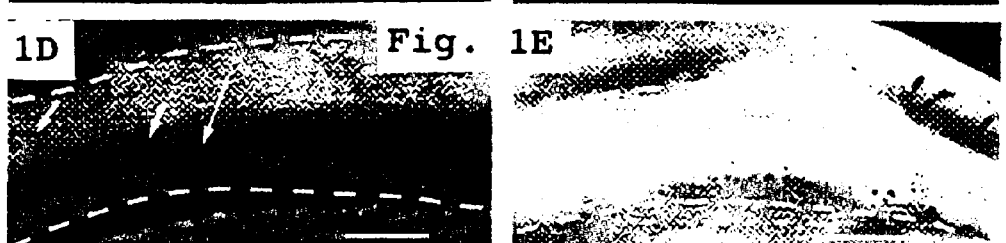
Figures 1F, 1G:
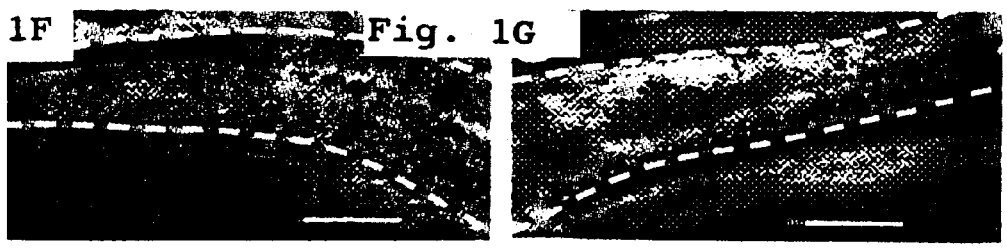
Figures 1H, 1I:
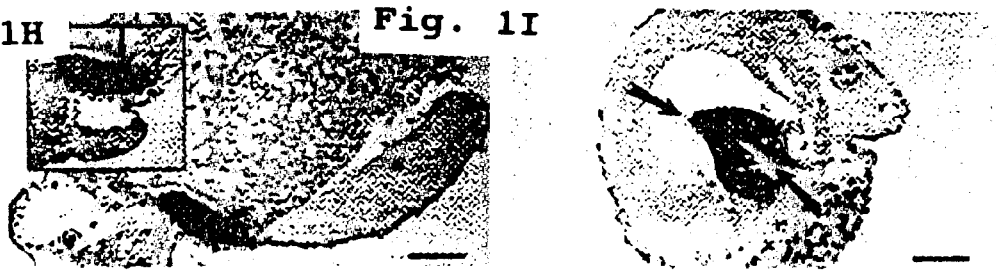

FIG. 1D shows a portion of the basilar papilla of a representative cochlear explant treated with forskolin. Numerous BrdU-labeled nuclei are seen across and along the sensory epithelium; some of these are paired suggesting that cell division has already occurred. Specificity controls using the inactive forskolin analog 1,9-dideoxy-forskolin did not show proliferation (data not shown). FIG. 1E shows the sensory epithelium of a cochlea treated with both forskolin and the PKA inhibitor KT5720. In this representative case, the number of BrdU-labeled nuclei is greatly diminished. Histologic cross-sections of treated explants were also prepared to demonstrate the location within the sensory epithelium of the labeled nuclei. FIG. 1H shows two examples of cochleas treated with forskolin. Multiple labeled nuclei are seen at the level of both supporting cells and hair cells. This is in contrast to the example of the untreated control cochlea shown in FIG. 1I, in which no labeled nuclei can be identified within the sensory epithelium. This set of experiments is summarized in FIG. 2A. Treatment with either forskolin or 8-bromo-cAMP was highly effective in stimulating DNA synthesis in the normally quiescent basilar papilla. Control papillas contained only one to three BrdU-labeled nuclei, while those treated with forskolin and 8-bromo-cAMP contained an average of 180 and 50, respectively. Forskolin-induced BrdU incorporation was reduced 87% and 73% by H89 and KT5729, respectively. These data show that stimulation of the cAMP pathway in the undamaged basilar papilla leads to proliferation, indicating that the key pathway components are present in sensory epithelial cells.

EXAMPLE II cAMP Is Involved in Stimulating Proliferation of Auditory Receptor Epithelium Following Gentamicin Damage A second set of experiments was performed to determine if the cAMP pathway is involved in the regenerative proliferation seen following gentamicin damage. Four groups of cochleas were explanted and cultured for four days in the presence of BrdU. The first group was undamaged, and served as a control. The second group was damaged with gentamicin in vitro in order to induce regenerative proliferation. The third and fourth groups were damaged with gentamicin and treated with the PKA inhibitors H89 and KT5720 to determine if blocking the cAMP-regulated protein kinase diminishes the damage-induced proliferative response. FIG. 1F shows a portion of the sensory epithelium from a cochlear explant damaged with gentamicin. BrdU-labeled nuclei are seen studding the epithelium. In contrast, concomitant treatment with H89 resulted in a decrease in the number of labeled cells as shown in FIG. 1G. This set of experiments is summarized in FIG. 2B. Under the conditions utilized here, gentamicin damage resulted in a level of DNA synthesis roughly equivalent to that induced in the undamaged basilar papilla by treatment with 8-bromo-cAMP and IBMX. The number of cells per basilar papilla induced to undergo DNA synthesis by gentamicin damage was reduced 61% and 77% by H89 and KT5720, respectively. These results provide evidence that the cAMP pathway is also involved in signaling the regenerative proliferation which follows damage due to aminoglycoside antibiotics.

EXAMPLE III

Receptor Hair Cells are Stimulated by Agents that Activate the cAMP Pathway

Figure 3A:
FIGS. 3A–3C are a series of autoradiographs showing $^3$H-thymidine labeling of sensory epithelial cells in cochlear explants stimulated with forskolin.
Figure 3B:
Figure 3C:
Figure 4:
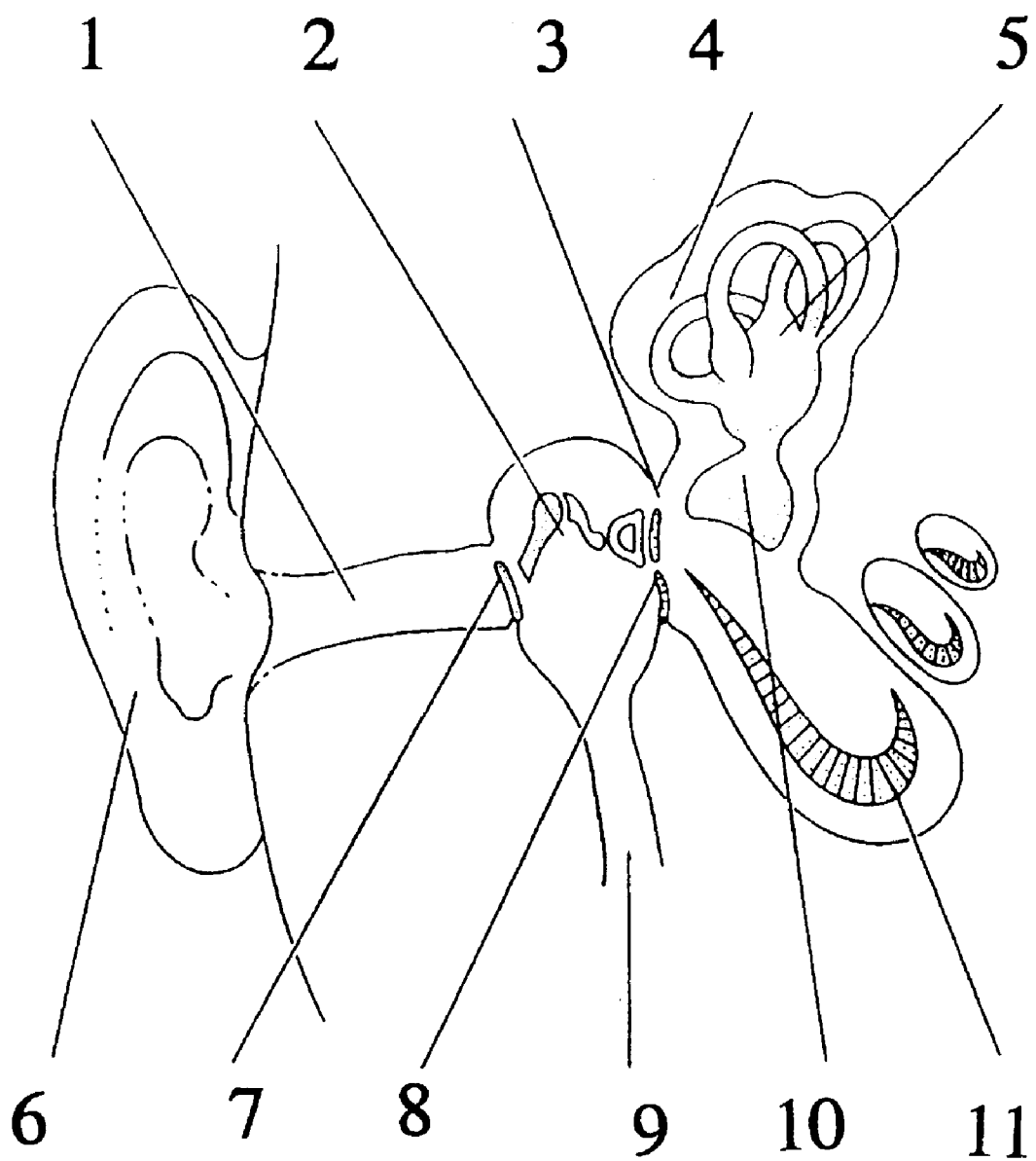
FIG. 4 is a schematic diagram of the mammalian inner ear.

A third set of experiments was performed to determine if the population of cells which become labeled with DNA synthesis markers after activation of the cAMP pathway includes receptor hair cells. Cochlear explants were treated with forskolin in the presence of $^3$H-thymidine, and autoradiography was performed on plastic-embedded cross-sections. For this set of experiments the explants were maintained in culture for five days rather than three to allow a longer time period for the presumptive differentiation of supporting cell progeny into hair cells (11). FIG. 3 shows representative portions of the sensory epithelium from three cochlear explants. Several examples of hair cells with clearly-labeled nuclei are seen; other labeled cells within the epithelium resembled supporting cells. Essentially every section examined contained multiple labeled sensory epithelial cells; most sections contained at least one labeled hair cell. These results suggest that the cAMP-induced proliferation leads to the production of new hair cells.

EXAMPLE IV

Treatment of Auditory Receptor Epithelium in Situ

The results presented implicate the involvement of the cAMP pathway in the regeneration of auditory receptor epithelium. Accordingly, hearing compromised patients would be treated with agents that stimulate cAMP production. Fo example, forskolin (25–100 μM dissolved in dimethylsulfoxide (DMSO)) in a suitable pharmaceutical carrier would be delivered via drops, injection or to the cochlea of the patient. Alternatively, the drug delivery system may comprise an osmotic pump or other timed-release gel delivery systems known in the art. Restoration of hearing would then be assessed using standard methods.

The methods performed in explant culture may also be performed in situ. In control experiments, ototoxic agents would be co-administered with agents for detecting DNA replication. After a predetermined time period the animal would be sacrificed and proliferation would be assessed. Agents that stimulate (i.e., cAMP activators) or abrogate (i.e., PKA inhibitors) the proliferative response may also be simultaneously administered to the animal and their effects assessed. These procedures would result in the further elucidation of the molecular mechanisms involved in the regeneration of auditory epithelium.

DISCUSSION

These studies are the first to show induction of proliferation in the normally quiescent auditory sensory epithelium by any means other than damage. Moreover, damage-induced proliferation can be blocked with inhibitors of the cAMP pathway. Stimulation of proliferation in the vestibular epithelium, which normally exhibits a basal rate of proliferation (15), has been reported in response to several "traditional" growth factors (16,17). cAMP-mediated stimulation of proliferation is unusual, but not unprecedented (18). It is also becoming increasingly recognized that cross-talk occurs between the cAMP pathway and the growth factor mitogenic pathway (19). Whatever form such potential interactions might take, the identification of the cAMP pathway as playing an important role in signaling proliferation in the undamaged cochlear sensory epithelium, as well as in regenerative proliferation following damage, suggests a rational direction for those therapeutic approaches to hearing loss which are aimed at the production of new receptor hair cells.

REFERENCES

1. Nadol, J. B.,Jr. Hearing loss. N. Engl. J. Med. 329, 1092–1102 (1993).
2. Corwin, J. T. & Cotanche, D. A. Regeneration of sensory hair cells after acoustic trauma. Science 240, 1772–1774 (1988).
3. Ryals, B. M. & Rubel, E. W. Hair cell regeneration after acoustic trauma in adult Coturnix quail. Science 240, 1774–1776 (1988).
4. Lippe, W. R., Westbrook, E. W. & Ryals, B. M. Hair cell regeneration in the chicken cochlea following aminoglycoside toxicity. Hear. Res. 56, 203–210 (1991).
5. Cotanche, D. A., Lee, K. H., Stone, J. S., et al. Hair cell regeneration in the bird cochlea following noise damage or ototoxic drug damage. Anat. Embryol. (Berl). 189, 1–18 (1994).
6. Girod, D. A., Duckert, L. G. & Rubel, E. W. Possible precursors of regenerated hair cells in the avian cochlea following acoustic trauma. Hear. Res. 42, 175–194 (1989).
7. Corwin, J. T., Jones, J. E., Katayama, A., et al. Hair cell regeneration: the identities of progenitor cells, potential triggers and instructive cues. Ciba. Found. Symp. 160, 103–20 (1991).
8. Raphael, Y. Evidence for supporting cell mitosis in response to acoustic trauma in the avian inner ear. J. Neurocytol. 21, 663–671 (1992).
9. Hashino, E., Tanaka, Y., Salvi, R. J., et al. Hair cell regeneration in the adult budgerigar after kanamycin ototoxicity. Hear. Res. 59, 46–58 (1992).
10. Hashino, E. & Salvi, R. J. Changing spatial patterns of DNA replication in the noise-damaged chick cochlea. J. Cell Sci. 105, 23–31 (1993).
11. Stone, J. S. & Cotanche, D. A. Identification of the timing of S phase and the patterns of cell proliferation during hair cell regeneration in the chick cochlea. J. Comp. Neurol. 341, 50–67 (1994).
12. Bhave, S. A., Stone, J. S., Rubel, E. W., et al. Cell cycle progression in gentamicin-damaged avian cochleas. J. Neurosci. 15, 4618–4628 (1995).
13. McFadden, E. A. & Saunders, J. C. Recovery of auditory function following intense sound exposure in the neonatal chick. Hear. Res. 41, 205–215 (1989).
14. Tucci, D. L. & Rubel, E. W. Physiologic status of regenerated hair cells in the avian inner ear following aminoglycoside ototoxicity. otolaryngol. Head Neck Surg. 103, 443–450 (1990).
15. Jorgensen, J. M. & Mathiesen, C. The avian inner ear. Continuous production of hair cells in vestibular sensory organs, but not in the auditory papilla. Naturwissenschaften 75, 319–320 (1988).
16. Lambert, P. R. Inner ear hair cell regeneration in a mammal: identification of a triggering factor. Laryngoscope 104, 701–718 (1994).
17. Yamashita, H. & Oesterle, E. C. Induction of cell proliferation in mammalian inner-ear sensory epithelia by transforming growth factor alpha and epidermal growth factor. Proc. Natl. Acad. Sci. U.S.A. 92, 3152–3155 (1995).
18. Dumont, J. E., Jauniaux, J. C. & Roger, P. P. The cyclic AMP-mediated stimulation of cell proliferation. Trends Biochem. Sci. 14, 67–71 (1989).
19. Marx, J. Two major signal pathways linked. Science 262, 988, 990 (1993).
20. Oesterle, E. C., Tsue, T. T., Reh, T. A., et al. Hair-cell regeneration in organ cultures of the postnatal chicken inner ear. Hear. Res. 70, 85–108 (1993).
21. Forge, A. & Richardson, G. Freeze fracture analysis of apical membranes in cochlear cultures: differences between basal and apical-coil outer hair cells and effects of neomycin. J. Neurocytol. 22, 854–867 (1993).
22. Bartolami, S., Goodyear, R. & Richardson, G. Appearance and distribution of the 275 kD hair-cell antigen during development of the avian inner ear. J. Comp. Neurol. 314, 777–788 (1991).
23. Oberholtzer, J. C., Buettger, C., Summers, M. C., et al. The 28-kDa calbindin-D is a major calcium-binding protein in the basilar papilla of the chick. Proc. Natl. Acad. Sci. U.S.A. 85, 3387–3390 (1988).
24. Dartt, D. A., Donowitz, M., Joshi, V. J., et al. Cyclic nucleotide-dependent enzyme secretion in the rat lacrimal gland. J. Physiol. (Lond). 352, 375–384 (1984).
25. Hentrich, F., Gothert, M. & Greschuchna, D. Involvement of cAMP in modulation of noradrenaline release in the human pulmonary artery. Naunyn Schmiedebergs. Arch. Pharmacol. 330, 245–247 (1985).
26. Zheng, J. L., Helbig, C. & Gao, W-Q. Induction of cell proliferation by fibroblast and insulin-like growth factors in pure rat inner ear epithelial cell cultures. J. Neurosci. 17:216–226 (1997).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for stimulating regeneration of receptor hair cells by augmenting cAMP levels, comprising:
   a) preparing hair cell epithelial explant cultures; and
   b) administering an agent which activates the cAMP pathway to said explant culture, said agent being an adenylate cyclase stimulator, thereby inducing proliferation in adjacent supporting cells, said supporting cells differentiating into replacement receptor hair cells.

2. A method according to claim 1, wherein said receptor hair cells are of avian origin.

3. A method according to claim 1, wherein said receptor hair cells are of mammalian origin.

4. The method of claim 1, wherein said adenylate cyclase stimulator is selected from the group consisting of 8-bromo-cAMP and forskolin.

5. A method for augmenting cAMP levels in receptor hair cell epithelia comprising administration of an agent selected from the group consisting of cAMP and at least one cAMP analogue.

6. A method for restoring hair cells in damaged receptor epithelia, comprising:
   a) preparing hair cell epithelia explant cultures;
   b) administering an ototoxic agent which results in a measurable loss of hair cells, said ototoxic agent being selected from the group consisting of aminoglycoside antibiotics, chemotherapeutic agents, and sound pressure levels exceeding 80 decibels;
   c) administering an agent which activates the cAMP pathway, said agent being an adenylate cyclase stimulator, to said damaged epithelia, and an agent for detecting DNA replication in said cultures, said agent for detecting DNA replication being selected from the group consisting of bromo-deoxyuridines, at least one fluoresceinated nucleotide, and at least one radioactive nucleotide; and
   d) measuring restoration of hair receptor cells by assaying incorporation of said DNA replication agent into said receptor cells.

7. A method according to claim 6, wherein said hair receptor cells are of avian origin.

8. A method according to claim 6, wherein said hair receptor cells are of mammalian origin.

9. The method of claim 6, wherein said aminoglycoside antibiotic is gentamycin.

10. The method of claim 6, wherein said chemotherapeutic agent is cisplatin.

11. The method of claim 6, wherein said adenylate cyclase stimulator is selected from the group consisting of 8-bromo-cAMP and forskolin.

12. A method for treating a patient with compromised hearing, comprising:
   a) administering to said patient an agent which activates the cAMP pathway, said agent being an adenylate cyclase stimulator; and
   b) assessing said patient for restoration of hearing.

13. A method for treating a patient with compromised hearing, comprising: administering forskolin in a range of 1–200 $\mu$M to said patient's auditory receptor epithelium in a pharmaceutically acceptable carrier, thereby stimulating regeneration of said receptor epithelium.

14. The method according to claim 12, wherein said cAMP activating agent is delivered by a delivery means selected from the group consisting of local injection, ear drops, osmotic pumping and timed release delivery systems.

15. A method for treating a hearing compromised patient according to claim 12, wherein said patient is an animal and hearing restoration is correlated with demonstrable regrowth of auditory receptor hair cells.

16. The method of claim 12, wherein said adenylate cyclase stimulator is selected from the group consisting of 8-bromo-cAMP and forskolin.

17. A method for stimulating regeneration of receptor hair cells by augmenting cAMP levels, comprising:
   a) preparing hair cell epithelial explant cultures;
   b) administering an agent which activates the cAMP pathway, said agent being an adenylate cyclase stimulator, thereby inducing proliferation in adjacent supporting cells, said supporting cells differentiating into replacement receptor hair cells; and
   c) determining the extent of regeneration of receptor hair cells as a function of incorporation of an agent which detectably labels DNA.

18. A method as claimed in claim 17, wherein said agent which detectably labels DNA is selected from the group consisting of bromo-deoxyuridine, at least one fluoresceinated nucleotide, and at least one radioactive nucleotide.

19. The method of claim 17, wherein said adenylate cyclase stimulator is selected from the group consisting of 8-bromo-cAMP and forskolin.

* * * * *